United States Patent
Stewart et al.

(10) Patent No.: US 7,155,393 B2
(45) Date of Patent: Dec. 26, 2006

(54) METHOD FOR ESTABLISHING FIXATION EMPLOYING SPEECH RECOGNITION

(75) Inventors: Jeffrey L. Stewart, Greenwich, CT (US); Stewart Weiss, Jackson Heights, NY (US)

(73) Assignee: Visionrx, LLC, Greenwich, CT (US)

( * ) Notice: Subject to any disclaimer, the term of this patent is extended or adjusted under 35 U.S.C. 154(b) by 796 days.

(21) Appl. No.: 09/973,453

(22) Filed: Oct. 9, 2001

(65) Prior Publication Data

US 2003/0036907 A1 Feb. 20, 2003

Related U.S. Application Data

(60) Provisional application No. 60/313,311, filed on Aug. 18, 2001.

(51) Int. Cl.
*G10L 21/00* (2006.01)
*A61B 3/024* (2006.01)

(52) U.S. Cl. ........................... 704/270; 351/224
(58) Field of Classification Search ............... 704/275, 704/271, 270; 351/246, 223, 226, 224; 251/237; 434/178
See application file for complete search history.

(56) References Cited

U.S. PATENT DOCUMENTS

| | | | | |
|---|---|---|---|---|
| 5,035,500 A | * | 7/1991 | Rorabaugh et al. | 351/226 |
| 5,465,982 A | * | 11/1995 | Rebane | 463/9 |
| 5,565,949 A | * | 10/1996 | Kasha, Jr. | 351/224 |
| 5,589,897 A | * | 12/1996 | Sinclair et al. | 351/223 |
| 5,737,060 A | * | 4/1998 | Kasha, Jr. | 351/224 |
| 5,801,810 A | * | 9/1998 | Roenker | 351/224 |
| 6,045,227 A | * | 4/2000 | Stewart et al. | 351/237 |
| 6,260,970 B1 | * | 7/2001 | Horn | 351/246 |
| 6,272,466 B1 | * | 8/2001 | Harada et al. | 704/270 |
| 6,350,128 B1 | * | 2/2002 | Neuhaus | 434/178 |

* cited by examiner

*Primary Examiner*—David Hudspeth
*Assistant Examiner*—James S. Wozniak
(74) *Attorney, Agent, or Firm*—John De La Rosa

(57) ABSTRACT

The present invention provides a method for establishing fixation during computerized visual field perimetry, requiring the subject to verbally identify the symbol employed as fixation targets as they each appear. Speech recognition techniques are then employed to evaluate the subject's response, and, upon correctly identifying the fixation symbol, a visual test stimulus is displayed at a predetermined location within the subject's field of vision. Fixation is established by displaying to the subject fixation targets represented by varying symbols, which may be displayed at one or more locations on a display monitor. These so-called fixation symbols, include geometrical shapes, letters, numbers, pictures or other symbols readily identifiable by the subject. When a fixation symbol appears, the subject verbally identifies the symbol by saying the name of the symbol into a microphone. Using speech recognition, the system recognizes the response from the subject, and evaluates whether the symbol was correctly identified by the subject. Upon being correctly identified, the fixation symbol disappears, and a flashing visual test stimulus is displayed within the subject's field of view for a preset time.

37 Claims, 1 Drawing Sheet

METHOD FOR ESTABLISHING FIXATION EMPLOYING SPEECH RECOGNITION

This application claims the benefit of U.S. Provisional Application No. 60/313,311 filed Aug. 18, 2001, entitled "Method For Establishing Fixation Employing Speech Recognition" which is incorporated herein by reference.

TECHNICAL FIELD

The present invention relates to a method for measuring a person's field of vision and, more particularly, to a method for establishing fixation during computerized visual field perimetry.

BACKGROUND OF THE INVENTION

A large number of degenerative eye disorders, such as glaucoma and macular degeneration, may be detected by evaluating a subject's visual field, such as through visual field perimetry. In visual field perimetry, a subject's eye is typically fixated on a stationary target (a "fixation point") while visual test stimuli are displayed momentarily within the subject's visual field. The subject's visual field is then mapped by recording his/her response to each visual test stimulus. To reduce eye fatigue, however, various methods have been developed which use instead a moving fixation point. With respect to such a moving fixation point, selected patents as discussed herein below are of interest, and are incorporated herein by reference.

In U.S. Pat. No. 4,995,717, a fixation point is moved around a computer screen while the subject attempts to track its movement by means of a computer mouse. More particularly, the subject moves the cursor, such as a circle, by means of the mouse to keep the fixation point surrounded by the cursor. Fixation is maintained while the cursor is surrounding the fixation point, allowing test stimuli to then be displayed within the subject's peripheral vision.

In U.S. Pat. No. 5,565,949, a fixation point again is moved around a computer screen, but during its movement it changes shape, for example, from a circle to a square, or vice a versa. After such a change in the fixation point, the subject is required to press a mouse button. Failure to respond to the change indicates a loss of fixation.

In U.S. Pat. No. 5,737,060, a moving fixation point, such as in the shape of an ant, is displayed on two independent screens of virtual reality glasses, which are worn by the subject. The fixation point is moved around the display screen of the glasses, with its overall direction of movement being clockwise. Two methods of monitoring fixation are used. In one, the subject must respond to changes in the direction of the fixation point though the use of a computer mouse. Any change in direction which the subject does not respond to is considered a loss of fixation. In the second method, blindspot monitoring is used as the fixation control. In this latter case, a target is displayed in the subject's blindspot on one of the display screens, while the fixation point is displayed on the other screen. If the subject responds to the blindspot target, then there is a loss of fixation since the blindspot target should not have been seen. Otherwise, it is assumed that fixation has been maintained.

Although computerized visual field perimetry systems satisfactorily employ fixation methods, whether stationary or moving, as discussed above herein, it would be desirable to have a method and system for establishing fixation which is less complicated, and can function using speech recognition as the method of input for the entire test. Morever, may fixation methods typically require costly equipment, such as the use of video cameras and eye tracking instruments. As such, it would be further desirable to have a method and system for establishing fixation which is less costly.

SUMMARY OF THE INVENTION

The present invention provides a method for establishing fixation during computerized visual field perimetry using speech recognition as the input method for responding to visual test stimuli. It requires the subject to verbally identify the symbols employed as fixation targets as they each appear. Voice recognition techniques are then employed to evaluate the subject's response, and upon correctly identifying the fixation symbol, a visual test stimulus is displayed at a predetermined location within the subject's visual field. With the fixation symbol varying with each visual test stimulus displayed to the subject, a mapping of the subject's visual field is obtained while assuring fixation, and without the need of any additional input devices, other than speech recognition.

In a preferred embodiment, fixation is established by displaying to the subject fixation targets represented by varying symbols, which may be displayed at one or more location on a display monitor. These so-called fixation symbols, include geometrical shapes, letters, numbers, pictures or other symbols readily identifiable by the subject. When a fixation symbol appears, the subject verbally identifies the symbol by saying the name of the symbol into a microphone, e.g., "X," "O," "square," "triangle," among other symbols. Using speech recognition, the system recognizes the response from the subject, and evaluates whether the symbol was correctly identified by the subject. Well known isolation word recognition techniques can be used to evaluate the subject's response. Upon being correctly identified, the fixation symbol disappears, and a flashing visual test stimulus is displayed within the subject's field of view for a preset time. Preferably, the visual test stimulus appears rapidly after the correct identification of the fixation symbol.

If the subject observes the flashing visual test stimulus, he/she response by saying "yes" and, the system pauses for a short time. This is repeated with different, randomly selected fixation symbols which may be located at the same place or moved to different locations in order to broaden the area of coverage tested on the retina. This series of steps is repeated until all preprogrammed locations determined by the type of visual field perimetry are performed.

The need to observe the fixation symbol while verbally identifying the symbol establishes fixation. This is so, since it is unlikely that the subject can correctly identify the fixation symbol if he/she is looking away from the fixation symbol. Once fixation has been established, the subject's eye is unlikely to wander before the flashing test stimulus is displayed since the identification and visual stimulus display occur in rapid sequence.

BRIEF DESCRIPTION OF THE DRAWINGS

The features and advantages of the present invention will become more readily apparent from the following detailed description of the invention in which like elements are labeled similarly and in which.

DETAILED DESCRIPTION

Figure 1:
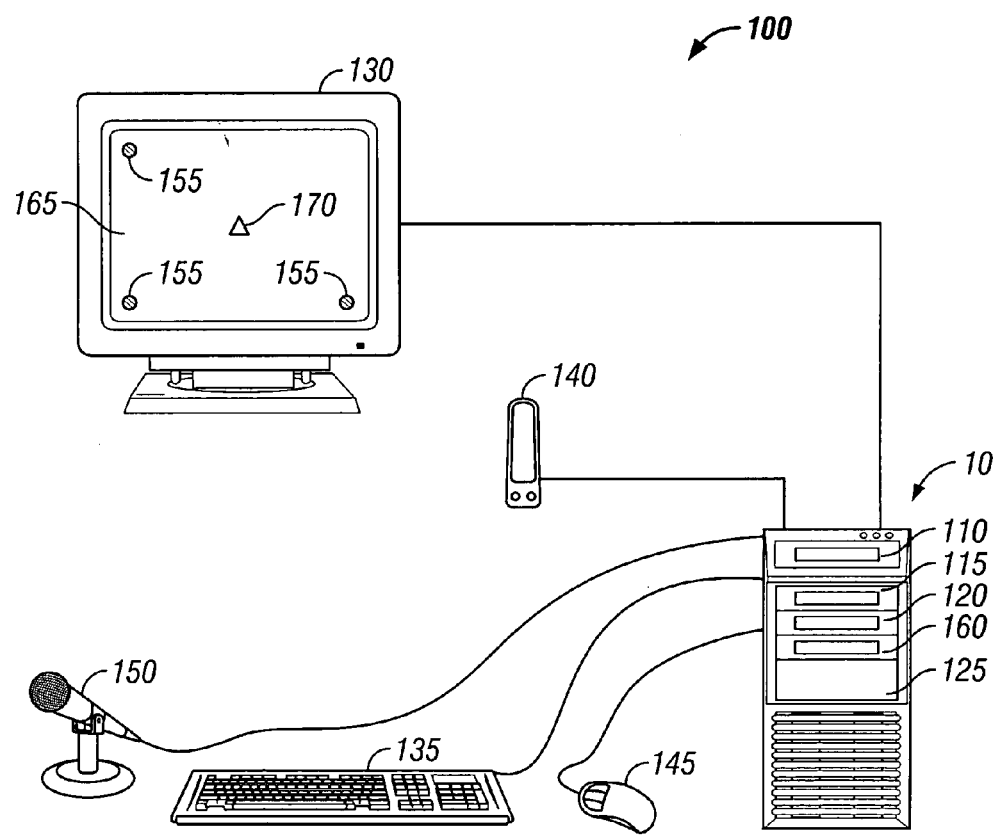
FIG. 1 is an exemplary diagram of a visual field perimetry system employing the present method of establishing fixation.

In visual field perimetry, a subject's eye is typically fixated on a target (a "fixation target"), while visual test stimuli are displayed within the subject's visual field. The subject's visual field is then mapped by recording the subject's response to each visual test stimulus, i.e., whether or not the subject observed the visual test stimulus. To increase area of coverage and increase the likelihood of fixation, various methods have been developed which, however, use a moving fixation point. This typically requires that a computer mouse be moved continuously during testing, as discussed herein above, which is difficult for some people, such as the disabled or elderly, and does not lend itself to the use of speech recognition. Morever, some fixation methods require costly equipment, such as the use of video cameras and eye tracking instruments.

The present invention is directed to a method for establishing fixation during computerized visual field perimetry that is less costly, and less complicated than the prior art. This is uniquely accomplished by requiring the subject to verbally identify the symbol employed as fixation targets as they each appear. Speech recognition techniques are then employed to evaluate the subject's response, and, upon correctly identifying the fixation symbol, a visual test stimulus is displayed at a predetermined location within the subject's field of view. With the fixation symbol varying with each visual test stimulus displayed to the subject, fixation is assured while mapping of the subject's visual field is obtained.

In accordance with the principles of the invention, there is shown in FIG. 1 a visual field perimetry system 100 implemented using a conventional computer system 105, including a CPU 110, ROM 115, RAM 120, a hard disk drive 125, a display monitor 130, a keyboard 135, a speaker 140, and a mouse 145. To effect user interaction, a microphone 150 is provided for the subject to respond to observed visual test stimuli 155 and, more importantly, to establish fixation. If desired, audible instructions to the subject may be communicated through speaker 140 during testing.

Preferably, the subject views display monitor 130 at a predetermined distance (e.g., 16") such that each visual test stimulus 155 subtends a predetermined angle, but of appropriate distance to test a preset solid angle of the subject's visual field, such as 60 degrees. Of course, the subject views visual test stimuli 155 monocularly, with each eye tested separately. The locations of visual test stimuli 155 within the visual field are chosen to suit different testing requirements.

As is well known in the art, to obtain a mapping of the subject's visual field or peripheral vision, the subject's central vision is fixated while visual test stimuli 155 are displayed in a random fashion at different locations within the subject's visual field. Visual test stimuli 155 should be displayed only once it has been established that the subject's eye is fixated. Visual test stimuli 155 are represented by pixels on the screen of display monitor 130, and are sent from a video controller 160 within computer system 105 to display monitor 130. Of course, other means may be used to generate the visual stimuli, such as discreet LEDs, or incandescent lights. In addition to displaying visual test stimuli 155, computer system 105 monitors the subject's response which is entered by the subject speaking into the microphone, such as by saying "yes" or some other verbal response so as to indicate that the visual test stimulus was observed by the subject.

Well known speech recognition techniques are employed for the computer system to understand the subject's response, including the use of isolation word recognition techniques for predetermined vocabularies. Speech recognition software employing such latter techniques may be stored on hard disk drive 125 and loaded into RAM 120 upon execution. The use of speech recognition allows those subjects unfamiliar with computers or unable to manually operate input devices to respond to the visual stimuli displayed to them.

Such speech recognition techniques can also be employed to evaluate the verbal identification of the visual test stimulus made by the subject.

Once the subject's eye is fixated, it is possible to conduct computerized visual field perimetry so as to assess the subject's visual field. More specifically, the perimeter corresponding to viewable area 165 of display monitor 130 is provided with a fixation target 170 (shown herein as a triangle) along with visual test stimuli 155 displayed at preprogrammed locations within the subject's visual field, i.e., viewable area 165. Computer 105 records the subject's verbal response to visual test stimuli 155 so as to map the subject's visual field, and may adjust the intensity levels or saturation levels of visual test stimuli 155 to determine precisely the threshold levels at which the stimuli are observed. From the resulting analysis of the visual field mapping, an operator is able to recognize abnormalities in the subject's eye.

Each visual test stimulus 155 can have a number of attributes, which can be programmed. These include: shape, intensity, size, color, contrast, frequency and duration of the stimulus. Also, the visual test stimulus can consist of visual patterns, such as sinusoidal gratings and oscillating frequency stimuli. Likewise, fixation target 170 can have a different shape, intensity, size, and color. The display format of visual test stimuli 155 and fixation target 170 is controlled by the graphics generator of the computer. For example, the visual test stimulus may have the shape of a small red circle to make it readily observable by the subject.

Also, it is contemplated that the visual test stimuli may employ the use of alternating complementary or counter-phase color visual stimuli, or color frequency doubling stimuli as disclosed in U.S. Pat. Nos. 6,227,668 and 6,608,377, respectively, which are incorporated herein by reference.

The computer system for the visual field perimetry establishes fixation by displaying to the subject fixation targets 170 which are represented by varying symbols, or so-called "fixation symbols." These fixation symbols may be displayed at one or more locations on display monitor 130, and include geometrical shapes, letters, numbers, pictures or other symbols readily identifiable by the subject. In FIG. 1, the symbol used as the fixation target is a triangle. Preferably, the fixation symbols subtend about 1–2 degrees. When a fixation symbol appears, the subject verbally identifies the symbol by saying the name of the symbol into the microphone, e.g., "X," "O," "square," "triangle" or "circle" among other symbols. Using speech recognition, the computer system recognizes the response from the subject, and evaluates whether the symbol was correctly identified by the subject. Again, well known isolation word recognition techniques can be used to evaluate the subject's response. Upon being correctly identified, the fixation symbol disappears, and flashing visual test stimulus 155 is displayed within the subject's field of view for a preset time, typically about ⅕ of a second. Preferably, visual test stimulus 155 appears rapidly after the correct identification of the fixation symbol.

It is contemplated that the speech recognition techniques be implemented so as to permit the system to adjust for the particular sound level, speech pattern, and tone of the subject, and use of different types and styles of microphones. Additionally, the confidence level of the speech recognition may be adjusted to set the level of certainty with which the system recognizes the word spoken by the subject. A high level of confidence would mean that the system requires a high level of certainty, meaning few errors, but may require more attempts before the word spoken by the subject is recognized.

The need to observe the fixation symbol while verbally identifying the symbol assures that fixation is established. This is so, since it is unlikely that the subject can correctly identify the fixation symbol if he/she is looking away from the fixation symbol. Once fixation has been established, the subject's eye is unlikely to wander before flashing test stimulus 155 is displayed since the identification and visual stimulus display occur in rapid sequence.

It is contemplated that the fixation symbol can be either maintained at a predetermined location, such as the center of display monitor 130, or moved to different locations on the computer screen while the subject attempts to correctly identify the symbol used as the fixation target.

Alternatively, a predetermined symbol may be used as the fixation target and moved around the display screen. To establish fixation, the subject must verbally indicate any changes in the direction of the fixation symbol, with any change in direction to which the subject does not respond considered a loss of fixation. Or, the fixation target during its movement may change symbols, such as from a "X" to "O," or from a "circle" to a "triangle," with the subject required after such a change to verbally identify the new symbol. Failure to correctly identify the new symbol employed as the fixation target indicates a loss of fixation.

If the subject observes flashing visual test stimulus 155, he/she responds by saying "yes" or some other command, and, after a slight pause, a different symbol is employed as fixation target 170 and appears, preferably at randomly selected positions on viewable area 165. Preferably, fixation symbol 170 appears on different areas of the display monitor in the following sequence: center, top, bottom left, top left, top right, and bottom right in order to provide a greater area of test coverage of the retina. Again, the subject must correctly identify the new fixation symbol 170 and say its name into the microphone. Fixation is again established by the subject correctly identifying the symbol, and flashing visual test stimulus 155 is then displayed at another point within the subject's visual field. The visual stimuli are displayed in this latter manner at all preprogrammed locations, which are determined by the type of visual field perimetry performed.

If the subject fails to correctly identify the fixation symbol after a preset number of tries, a different symbol may be displayed before the flashing visual test stimulus is displayed to the subject. Recall that the need to verbally identify the symbol assures fixation.

If the subject fails to respond to visual test stimulus 155 within a preset time, it is recorded as "missed." If the subject utters "yes" when no visual test stimulus is displayed, this is assumed to be a false positive. Missed stimuli, if desired, can be retested at the same parameter settings, e.g., intensity, to verify that the subject is unable to visualize the stimuli, or retested at a greater setting to assess the depth of the visual defect. The duration between successive visual test stimuli is determined by the subject's attention to correctly identify the fixation symbol. This allows the test to proceed at a pace which is established by the subject and thus eliminates anxiety created by current tests that proceed at a system generated rate.

Using accepted standards of automated perimetry, it is preferable to display visual test stimuli 155 at each of the 54 grid points of the standard 24-2 test pattern, wherein each grid point is spaced about 6 degrees of visual field. The number of stimuli, their locations and the difference in intensity levels and other parameters, however, may be chosen in a different manner, depending on the test strategy that is to be employed. For example, a rudimentary visual field screening can be performed with about 18 visual test stimuli. Also, a "binary staircase" or "threshold" testing strategy can be used, depending on the number of visual field locations to be used and the desired test time.

Also, to ensure reliability in the subject's response, false-positive and false-negative visual test stimuli may be presented to the subject, such techniques being well known to those skilled in the art. In the former case, a blank stimulus is displayed, whereas in the latter a stimulus is displayed having an intensity higher than the one previously displayed and seen by the subject at the same visual field location.

Software to implement the above described visual field perimetry therefore include fixating the subject's eye as discussed herein above using varying symbols for the fixation targets, verbally identifying the symbol, displaying and varying the location and intensity and other parameters of visual test stimuli 155 if the symbol is correctly identified, recording whether the subject observed the visual test stimuli, and then mapping the visual field on the basis of the subject's responses. Such software is readily capable of implementation by those skilled in the art who have been equipped with the understanding of the operation of visual field perimetry, and may be written in $C^{++}$, or any other programming language. Of course, the test data for each subject can be displayed either in graphical or text format on display monitor 130, and/or saved on a hard disk, recalled for later use, imported into a database for statistical analysis, and/or transmitted to a remote location.

Accordingly, the present invention provides a method for establishing fixation, particularly useful when conducting computerized visual field perimetry. Although, the method is embodied in a stand alone computer system, the present fixation method is also equally applicable for use in computerized visual field perimetry conducted over the World Wide Web or in embedded applications, such as fully dedicated visual field analyzer instruments. As such, the embodiment discussed herein above is merely illustrative of the principles of the invention. Various modifications will become apparent to those skilled in the art from the foregoing description and accompanying figures. Such modifications are intended to fall within the scope of appended claims.

The invention claimed is:

1. A method for establishing fixation in a visual field perimeter, comprising the steps of:
    displaying to a subject a fixation target using a predetermined symbol;
    inputting the subject's verbal identification of what the predetermined symbol is that is displayed as the fixation target;
    evaluating the verbal identification of the predetermined symbol made by the subject using speech recognition; and
    upon the subject correctly identifying what the predetermined symbol is that is displayed as the fixation target, displaying a visual test stimulus to the subject at a predetermined location within the subject's field of vision.

2. The method of claim 1 further comprising the step of evaluating the verbal identification of the visual test stimulus made by the subject using speech recognition.

3. The method of claim 1 further comprising the step of repeatedly carrying out the steps above for different predetermined symbols.

4. The method of claim 1 further comprising the step of repeatedly carrying out the steps above while relocating the predetermined symbol to a new location.

5. The method of claim 1 wherein the fixation target is a stationary target.

6. The method of claim 1 further comprising the step of moving the fixation target within the field of vision of the subject.

7. The method of claim 1 wherein the visual test stimulus is displayed shortly after the subject correctly identifies the predetermined symbol.

8. The method of claim 1 wherein the predetermined symbol is a geometrical shape, letter, number, picture, or image that is readily identifiable by the subject.

9. The method of claim 1 further comprising the step of recording whether the subject observes the visual test stimulus.

10. The method claim 1 further comprising the step of varying the size, shape, intensity, contrast, frequency and/or color of the visual test stimulus.

11. A method for establishing fixation in a visual field perimeter, comprising the steps of:
displaying to a subject a fixation target using a first symbol;
moving the fixation target along a first direction within the subject's field of vision;
changing the direction of movement of said fixation target from said first direction to a second direction;
inputting the subject's verbal indication of the direction when the fixation target changes direction from said first to said second direction;
evaluating the subject's verbal indication using speech recognition that the fixation target changed direction; and
upon the subject correctly indicating when the fixation target changes direction from said first to said second direction, displaying a visual test stimulus to the subject at a predetermined location within the subject's field of vision.

12. The method of claim 11 further comprising the step of evaluating the verbal identification of the visual test stimulus made by the subject using speech recognition.

13. The method of claim 11 further comprising the step of repeatedly carrying out the steps above with the fixation target changed from said first symbol to a second symbol.

14. The method of claim 11 further comprising the step of repeatedly carrying out the steps above while relocating the fixation target to a new location.

15. The method of claim 11 wherein the visual test stimulus is displayed to the subject shortly after the subject correctly indicates when the fixation target changes direction from said first to said second direction.

16. The method of claim 11 wherein said first symbol is a geometrical shape, letter, number, picture, or image that is readily identifiable by the subject.

17. The method of claim 11 further comprising the step of recording whether the subject observes the visual test stimulus.

18. The method claim 11 further comprising the step of varying the size, shape, intensity, contrast, frequency and/or color of the visual test stimulus.

19. A method for establishing fixation in a visual field perimeter, comprising the steps of:
displaying to a subject a fixation target using a first symbol;
moving the fixation target within the field of vision of the subject;
changing the appearance of the fixation target from said first symbol to a second symbol;
inputting the subject's verbal indication that the fixation target changed from said first to said second symbol;
evaluating the subject's verbal indication using speech recognition that the fixation target changed from said first to said second symbol; and
upon the subject correctly indicating when the fixation target changed from said first to said second symbol, displaying a visual test stimulus to the subject at a predetermined location within the subject's field of vision.

20. The method of claim 19 further comprising the step of evaluating the verbal identification of the visual test stimulus made by the subject using speech recognition.

21. The method of claim 19 further comprising the step of repeatedly carrying out the steps above while relocating the fixation target to a new location.

22. The method of claim 19 wherein the visual test stimulus is displayed to the subject shortly after the subject correctly indicates when the fixation target changes from said first to said second symbol.

23. The method of claim 19 wherein said first and second symbols are geometrical shapes, letters, numbers, pictures, or images that are readily identifiable by the subject.

24. The method of claim 19 further comprising the step of recording whether the subject observes the visual test stimulus.

25. The method claim 16 further comprising the step of varying the size, shape, intensity, contrast, frequency and/or color of the visual test stimulus.

26. A visual field perimeter comprising a means for establishing fixation, said means for establishing fixation including:
a display monitor;
means for displaying on said display monitor a fixation target to a subject using a first symbol;
means for inputting the subject's verbal identification of said first symbol;
speech recognition means for evaluating the subject's verbal identification of what the first symbol is that is displayed as the fixation target; and
responsive to the subject correctly identifying what the first symbol is that is displayed as the fixation target, means for displaying a visual test stimulus to the subject at a predetermined location within the subject's field of vision.

27. The visual field perimeter of claim 26 further comprising means for evaluating the verbal identification of the visual test stimulus made by the subject using speech recognition.

28. The visual field perimeter of claim 26 further comprising means for changing the fixation target from said first symbol to a second symbol.

29. The visual field perimeter of claim 26 further comprising means for relocating the fixation target to a new location.

30. The visual field perimeter of claim 26 further comprising means for recording whether the subject observes the visual test stimulus.

31. The visual field perimeter of claim 26 wherein said means for recording includes voice recognition techniques for evaluating the subject's verbal response in indicating whether the visual test stimulus is observed.

32. The visual field perimeter of claim 26 wherein the fixation target is a stationary target.

33. The visual field perimeter of claim 26 further comprising means for moving the fixation target within the field of vision of the subject.

34. The visual field perimeter of claim 26 further comprising means for changing the direction of the fixation target.

35. The visual field perimeter of claim 26 wherein the visual test stimulus is displayed to the subject shortly after the subject correctly identifies the predetermined symbol.

36. The visual field perimeter of claim 26 wherein the predetermined symbol is a geometrical shape, letter, number, picture, or image that is readily identifiable by the subject.

37. The visual field perimeter of claim 26 further comprising means for varying the size, shape, intensity, contrast, frequency and/or color of the visual test stimulus.

* * * * *